US00PP08388P

United States Patent [19]

Akerboom

[11] Patent Number: Plant 8,388

[45] Date of Patent: Sep. 21, 1993

[54] ASTER PLANT NAMED MOTHER OF PEARL

[76] Inventor: Petrus J. F. Akerboom, Paradijsweg 61, 2461 TL, Ter Aar, Netherlands

[21] Appl. No.: 895,729

[22] Filed: Jun. 9, 1992

[51] Int. Cl.[5] ..... A01H 5/00

[52] U.S. Cl. ..... Plt./68.1

[58] Field of Search ..... Plt./68.1

*Primary Examiner*—James R. Feyrer

*Attorney, Agent, or Firm*—Foley & Lardner

[57] ABSTRACT

A distinct cultivar of aster plant named 'Mother of Pearl', characterized by its cupped capitulum form and daisy capitulum type, pinkish white ray floret color, strong, well branched flower stems, relatively large flowers, and its many flowers, borne on short pedicels.

1 Drawing Sheet

The present invention comprises a new and distinct cultivar of Aster L. hereinafter referred to by the cultivar name *1 Mother of Pearl*'.

'Mother of Pearl' is a product of a planned breeding program which had the objective of creating new perennial Aster cultivars for year-round commerical production having well branched flower stems, large flower (capitulum) size, good flower (capitulum) form and shape, and having superior vase-life of the cut flowers. Such traits in combination were not present or needed improvement in previously available commercial cultivars.

'Mother of Pearl' was originated from a hybridization made by the inventor P. Akerboom in a controlled breeding program in Ter Aar, The Netherlands, in 1987. The female parent of 'Mother of Pearl' was an unnamed *Aster pilosus* seedling. The male parent was an unnamed *Aster novi-belgii* seedling.

'Mother of Pearl' was discovered and selected as one flowering plant within the progeny of the stated parentage by the inventor P. Akerboom on Sep. 10, 1987 in a controlled environment in Ter Aar and identified as seedling No. 87.M.K.B.R.2.G.

The first act of asexual reproduction of 'Mother of Pearl' was accomplished when vegetative cuttings were taken from the initial selection in November 1987 in a controlled environment in Ter Aar by a technician working under formulations established and supervised by P. Akerboom.

Horticultural examination of selected units initiated in 1988 and 1989 has demonstrated that the unique combination of characteristics as herein disclosed for 'Mother of Pearl' are firmly fixed and are retained through successive generations of asexual reproduction.

'Mother of Pearl' has not been observed under all possible environmental conditions. The phenotype may vary significantly under different environmental conditions of temperature, light intensity and daylength, without, however, any variance in the genotype.

The following observations, measurements and comparisons describe plants grown in Ter Aar, The Netherlands, under greenhouse conditions which approximate those generally used in commercial greenhouse practice in this country. The following traits have been repeatedly observed and are determined to be basic characteristics of 'Mother of Pearl', which, in combination, distinguish this Aster as a new and distinct cultivar:

1. Cupped capitulum form.
2. Daisy capitulum type.

3. Pinkish white ray floret color.
4. Diameter across face of capitulum of 36 to 44 mm at maturity.
5. Strong, well branched flower stems.
6. Many capitula per synflorescence, borne on short pedicels.

The accompanying color photographic drawings show typical synflorescence of 'Mother of Pearl', with the colors being as nearly true as possible with illustrations of this type.

The photograph at the top of the sheet is a perspective view of 'Mother of Pearl' grown as a single stem cut spray Aster.

The photograph at the bottom is a top view of several mature flowers of 'Mother of Pearl'.

Of the commercial cultivars known to the inventor, the most similar to 'Mother of Pearl' is the patented variety 'Pink Butterfly', disclosed in U.S. Plant Pat. No. 7,401. Reference is made to attached Chart A, which compares certain characteristics of 'Mother of Pearl' to the same characteristics of 'Pink Butterfly'.

In comparison to 'Pink Butterfly', 'Mother of Pearl' has more vigorous growth, thicker and courser flower stems, bigger leaves, much larger flowers (capitula) of a lighter color, and more numerous ray florets. Similar traits are capitulum form and type, spray formation, photoperiodic light reaction, and equally long lasting vase-lifes.

When compared to the male parent's flower and flower stem characteristics, 'Mother of Pearl' is much easier to handle during harvesting, with *novi-belgii* cultivars typically displaying brittle and easy breaking flower heads and branching stems. 'Mother of Pearl' is absolutely free of these drawbacks.

In the following description color references are made to The Royal Horticultural Society Colour Chart. The color values were determined between 12:00 and 14:00 hours on Jun. 20, 1989 at Ter Aar, The Netherlands.

Classification:

*Botanical.*—*Aster pilosus* × *novi-belgii* cv 'Mother of Pearl'.

*Commercial.*—Very large daisy-like spray Aster perennial.

INFLORESCENCE

A. Capitulum:

*Form.*—Cupped.

*Type.*—Daisy.

*Diameter across face.*—36 to 44 mm.

*Arrangement.*—Raceme inflorescence.

B. Corolla of ray florets:

*Color (general tonality from a distance of three meters).*—White-pinkish.

*Color (upper surface).*—Closest to 76D, actual color is slightly darker than shown.

*Color (under surface).*—Closest to 76D, actual color is slightly darker than shown.

*Shape of floret.*—Apex acute; very long, elliptic, straight.

*Size of floret.*—17–18 mm long×5 mm wide.

*Number of ray florets.*—30–38.

C. Corolla of disc florets:

*Color (mature).*—Disc florets themselves are closest to 1C/1D; disc base is deeper yellow giving an overall deeper effect than floret color.

*Color (immature).*—Closest to 1C/1D.

*Diameter of disc.*—9–10 mm.

D. Reproductive organs:

*Androecium.*—Present on disc florets only; no pollen.

*Gynoecium.*—Present on both ray and disc florets.

PLANT

A. General appearance:

*Height.*—Tall; depends on light reaction. Under continuous long days it can grow up to two meters tall; medium branching.

B. Foliage:

*Color.*—RHS 147A-B yellow-green.

*Shape.*—Oblanceolate.

*Size.*—Lower leaves, length 135–180mm, short to medium; width 26–33 mm, very broad. Upper leaves, length 110 mm; width 19 mm.

*Margin.*—Entire.

*Arrangement.*—Alternate, with angle acute.

CHART A
Comparison of 'Mother of Pearl' and 'Pink Butterfly'

| Cultivar | MOTHER OF PEARL | PINK BUTTERFLY |
|---|---|---|
| Ray floret color | White-pinkish | Light Pink |
| Capitulum form and type | Cupped daisy | Cupped daisy |
| Spray formation | Compound | Compound |
| Pedicels | 6–40 mm long | 7–12 mm long |
| Diameter across face of capitulum | 36–44 mm | 29–32 mm |
| Number of ray florets | 30–38 | 23–25 |

I claim:

1. A new and distinct cultivar of aster plant named 'Mother of Pearl', as illustrated and described.

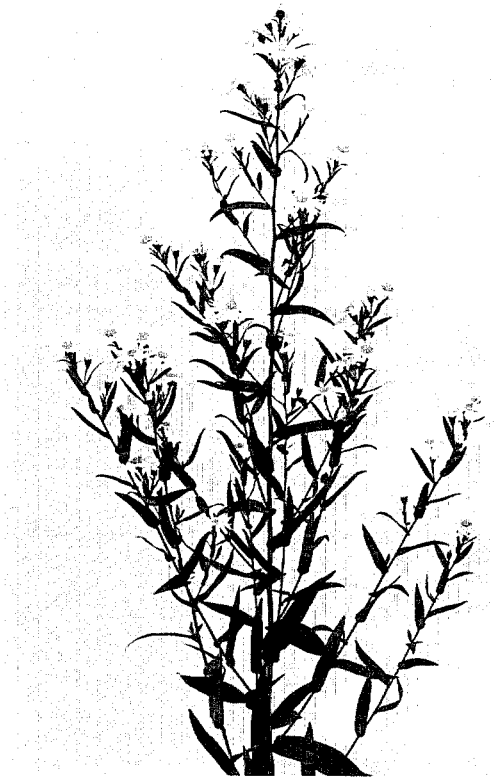
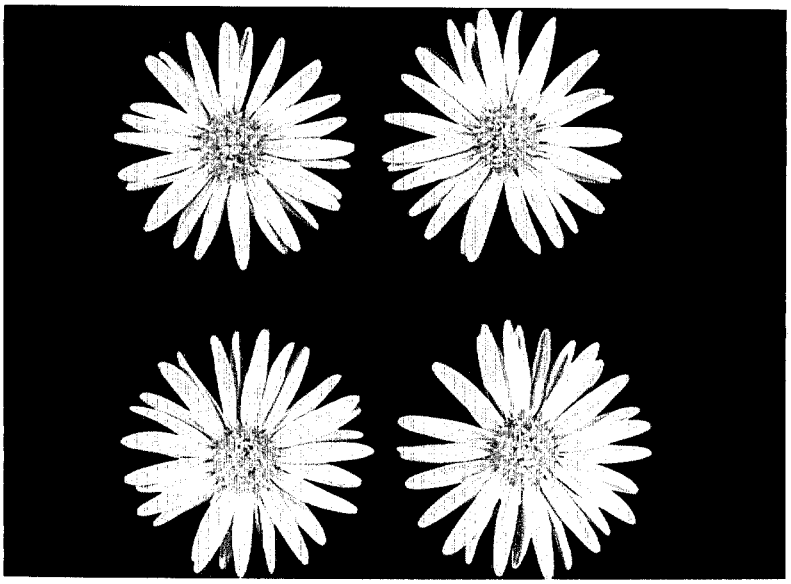

* * * * *